(12) United States Patent
Wu et al.

(10) Patent No.: US 9,878,208 B2
(45) Date of Patent: Jan. 30, 2018

(54) METHOD AND DEVICE FOR DETERMINING VALUE OF CONSUMED ENERGY

(71) Applicant: Xiaomi Inc., Beijing (CN)

(72) Inventors: Ke Wu, Beijing (CN); Xinyu Liu, Beijing (CN); Huayijun Liu, Beijing (CN)

(73) Assignee: Xiaomi Inc., Beijing (CN)

( * ) Notice: Subject to any disclaimer, the term of this patent is extended or adjusted under 35 U.S.C. 154(b) by 0 days.

(21) Appl. No.: 15/137,858

(22) Filed: Apr. 25, 2016

(65) Prior Publication Data

US 2017/0100631 A1    Apr. 13, 2017

(30) Foreign Application Priority Data

Oct. 12, 2015 (CN) .......................... 2015 1 0660649

(51) Int. Cl.
*A63B 24/00* (2006.01)
*A63B 21/00* (2006.01)
*A63B 23/02* (2006.01)

(52) U.S. Cl.
CPC ...... *A63B 24/0062* (2013.01); *A63B 21/4037* (2015.10); *A63B 23/0211* (2013.01); *A63B 23/0216* (2013.01)

(58) Field of Classification Search
CPC . A63B 24/00; A63B 24/0087; A63B 24/0062; A63B 23/0211; A63B 23/0216; A63B 21/4037; A63B 5/11
See application file for complete search history.

(56) References Cited

U.S. PATENT DOCUMENTS

| | | | |
|---|---|---|---|
| 2007/0293374 A1 | 12/2007 | Chan | |
| 2015/0321039 A1 | 11/2015 | Howe | |
| 2017/0080279 A1* | 3/2017 | Arredondo | A63B 21/4037 |

FOREIGN PATENT DOCUMENTS

| | | |
|---|---|---|
| CN | 1480233 A | 3/2004 |
| CN | 102068260 A | 5/2011 |
| CN | 103040473 A | 4/2013 |
| CN | 204192123 U | 3/2015 |
| CN | 104490399 A | 4/2015 |
| CN | 104548564 A | 4/2015 |
| CN | 104780264 A | 7/2015 |
| JP | H 08-336512 A | 12/1996 |
| JP | H 11-56818 A | 3/1999 |
| JP | 2006-247258 A | 9/2006 |
| JP | 2007061581 A | 3/2007 |
| JP | 2008-237832 A | 10/2008 |

(Continued)

OTHER PUBLICATIONS

Extended Search Report for European Application No. 16162083.6 from the European Patent Office, dated Feb. 24, 2017.

(Continued)

*Primary Examiner* — Glenn Richman
(74) *Attorney, Agent, or Firm* — Finnegan, Henderson, Farabow, Garrett & Dunner LLP

(57) ABSTRACT

A method for determining an amount of consumed energy includes acquiring deformation information of a mat surface of an elastic mat used by a user during one deformation process, determining an amount of energy consumed by the user during the deformation process according to the deformation information, and recording the amount of energy.

17 Claims, 8 Drawing Sheets

(56) References Cited

FOREIGN PATENT DOCUMENTS

| JP | 2011239892 A | 12/2011 |
| JP | 2013-544140 A | 12/2013 |
| JP | 2016-174699 A | 10/2016 |
| KR | 20140103145 A | 8/2014 |
| WO | WO 2014/098628 A1 | 6/2014 |

OTHER PUBLICATIONS

International Search Report in international application No. PCT/CN2015/098926, dated Jul. 19, 2016.

English language International Search Report issued by the State Intellectual Property Office of the People's Republic of China (SIPO) dated Jul. 19, 2016, in counterpart International Application No. PCT/CN2015/098926.

* cited by examiner

METHOD AND DEVICE FOR DETERMINING VALUE OF CONSUMED ENERGY

CROSS-REFERENCE TO RELATED APPLICATIONS

The present application is based on and claims priority to Chinese patent application No. 201510660649.0, filed on Oct. 12, 2015, the entire contents of which are incorporated herein by reference.

TECHNICAL FIELD

The present disclosure relates to computer technologies and, more particularly, to a method and device for determining an amount of consumed energy.

BACKGROUND

People have begun to pay attention to health problems with the continuous improvement of living standards, and most people like to keep fit by means of exercises. Generally, people can calculate an amount of energy consumed in an exercise to determine an amount of exercise.

In conventional technologies, when determining the amount of exercise, people generally record the name and a corresponding duration of a single exercise and then inquire an amount of energy that can be consumed in the exercise within a unit of time. For example, one minute of sit-up would consume 10 calories. Thus, the amount of energy consumed by the exercise can be calculated according to an exercise duration, and the amount of exercise can be determined accordingly.

However, with the conventional technologies described above, only the duration of the exercise is tracked for calculating the amount of consumed energy without considering the difference in energy consumption caused by different exercise amplitudes and exercise frequencies within the same period of time. Thus, the accuracy in calculating the amount of consumed energy is not accurate.

SUMMARY

In accordance with the present disclosure, there is provided a method for determining an amount of consumed energy. The method includes acquiring deformation information of a mat surface of an elastic mat used by a user during one deformation process, determining an amount of energy consumed by the user during the deformation process according to the deformation information, and recording the amount of energy.

Also in accordance with the present disclosure, there is provided an elastic mat including a processor and a memory storing instructions that, when executed by the processor, cause the processor to acquire deformation information of a mat surface of the elastic mat used by a user during one deformation process, determine an amount of energy consumed by the user during the deformation process according to the deformation information, and record the amount of energy.

Also in accordance with the present disclosure, there is provided a non-transitory computer-readable storage medium having stored therein instructions that, when executed by a processor of an elastic mat, cause the elastic mat to acquire deformation information of a mat surface of the elastic mat used by a user during one deformation process, determine an amount of energy consumed by the user during the deformation process according to the deformation information, and record the amount of energy.

It is to be understood that both the foregoing general description and the following detailed description are exemplary and explanatory only and are not restrictive of the present disclosure.

BRIEF DESCRIPTION OF THE DRAWINGS

The accompanying drawings, which are incorporated into and constitute a part of this specification, illustrate embodiments consistent with the embodiments of the present disclosure and, together with the description, serve to explain the principles of the embodiments of the present disclosure, in which.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the invention. Instead, they are merely examples of apparatuses and methods consistent with aspects related to the invention as recited in the appended claims.

Methods consistent with the present disclosure can be implemented, for example, in an elastic mat, such as, for example, an intelligent mattress or an intelligent yoga mat. The elastic mat can include a sensor, a processor, and a memory. The sensor is configured to detect deformation information of the surface of the elastic mat, and can be, for example, a displacement sensor. The processor is configured to determine an amount of consumed energy according to the detected deformation information. The memory is configured to store data required and generated during a process consistent with the present disclosure. The elastic mat can further include a communication component, a prompt component, and so on. The communication component is configured to transmit data. The prompt component is configured to send a prompt signal, and can include, for example, a loudspeaker, an indicator lamp, and/or a display screen.

Figure 1:
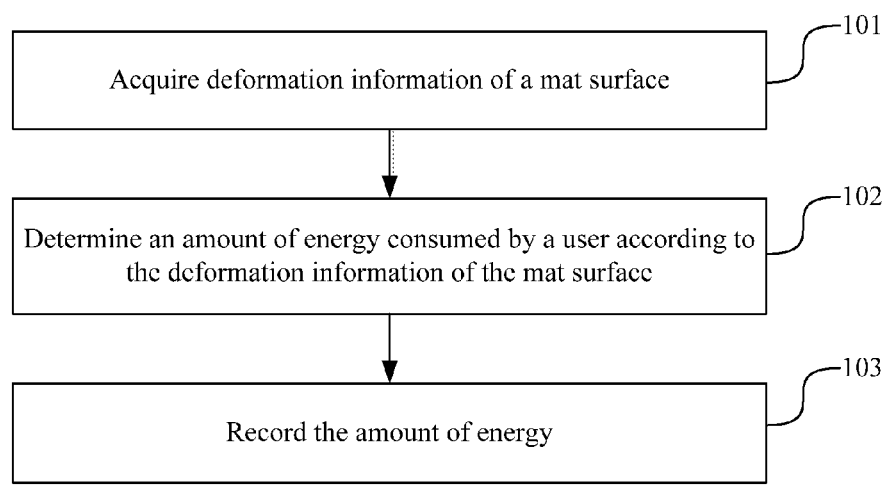
FIG. 1 is a flow chart showing a method for determining an amount of consumed energy according to an exemplary embodiment.
Figure 2:
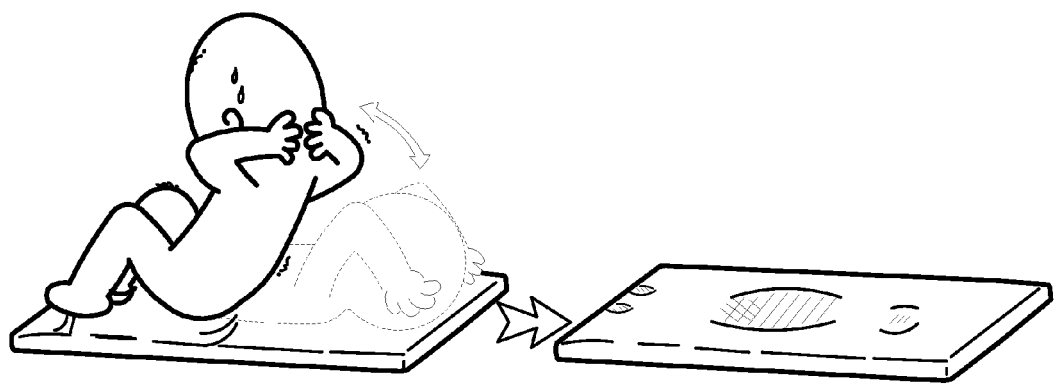
FIG. 2 is a schematic diagram illustrating a user exercising on an elastic mat according to an exemplary embodiment.

FIG. 1 is a flow chart showing a method for determining an amount of consumed energy according to an exemplary embodiment. As shown in FIG. 1, at 101, deformation information of the surface of the elastic mat, also referred to herein as a "mat surface," is acquired. FIG. 2 schematically shows a scenario in which a user does exercises on the elastic mat and presses the mat surface to deform. In some embodiments, the sensor in the elastic mat can detect and record the deformation information of the mat surface.

In some embodiments, the deformation information can include a deformation degree and a deformation duration of the mat surface at each of a plurality of preset detection points of the elastic mat. The deformation degree at a detection point refers to the distance from an initial position of the mat surface at the detection point to a maximum change position of the mat surface at the detection point during one deformation process. The deformation duration refers to a duration of time that the mat surface deforms from the initial position to the maximum change position at the detection point during one deformation process. For example, the deformation degree can be a displacement detected by a displacement sensor and the deformation duration can be a period of time required for the corresponding displacement. The initial position refers to a position where the mat surface at the detection point locates after the mat surface is deformed and stabilized when the user is on the surface of the elastic mat and is ready to do exercises. One deformation process can be one of the cyclic change processes in which the amount of deformation of the mat surface repeatedly increases and decreases.

Figure 3A:
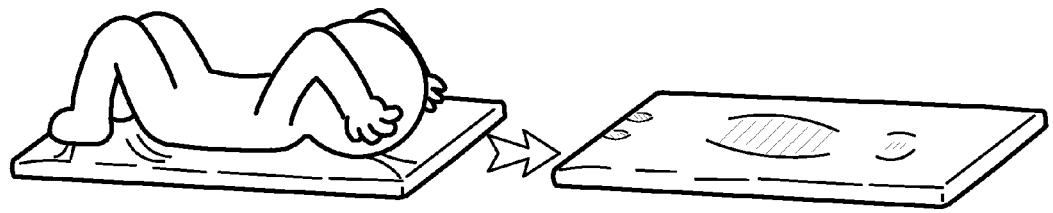
FIGS. 3a and 3b are diagrams illustrating a state of initial position according to an exemplary embodiment.
Figure 3B:
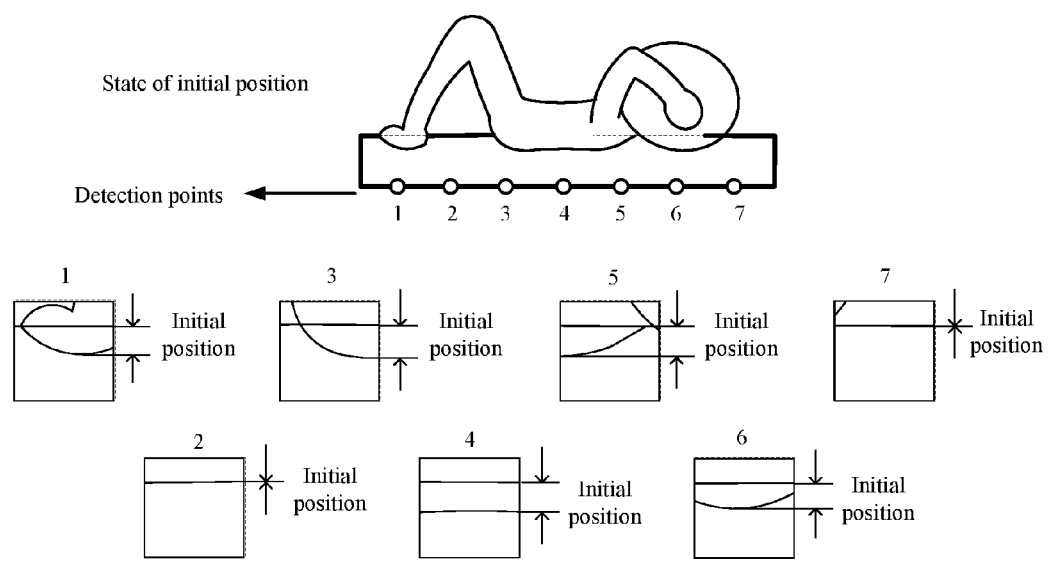

For example, FIG. 3a schematically illustrates a scenario in which the user lies on the elastic mat. The mat surface is pressed down to a certain degree due to the weight of the user. FIG. 3b schematically illustrates the deformation of the mat surface at various detection points when the elastic mat is in a stable state after the user lies down, i.e., when the user is in a lying state. The state of the elastic mat where the mat surface at the detection points is at the initial positions is also referred to herein as a "state of initial position." Specifically, as shown in FIG. 3b, a degree of pressing of the mat surface at each detection point is determined and recorded as the initial position of the mat surface at that detection point. Subsequently, the user begins to lift the upper half of the body to a sitting state.

Figure 4A:
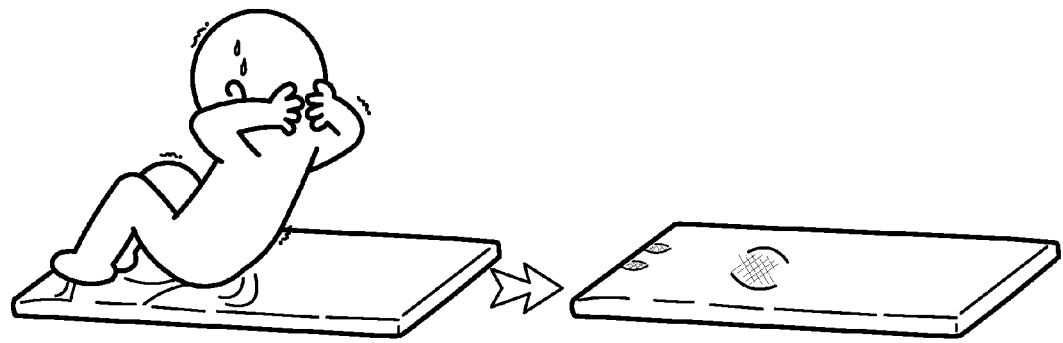
FIGS. 4a and 4b are diagrams illustrating a state of maximum change position according to an exemplary embodiment.
Figure 4B:
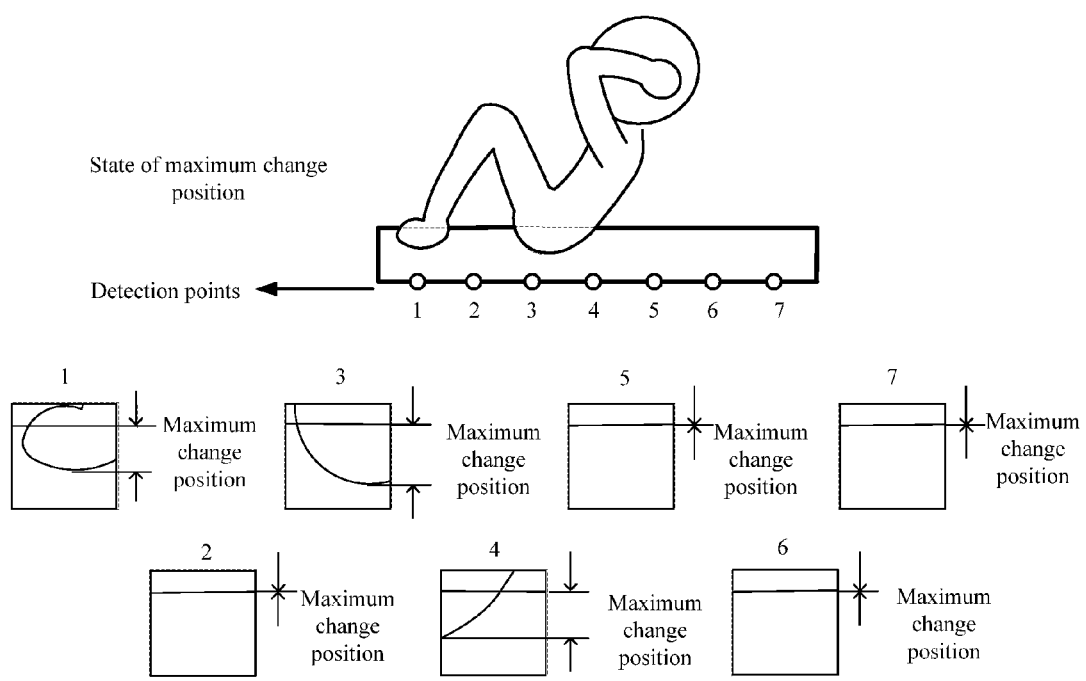

FIG. 4a schematically illustrates the scenario where the user is in the sitting state. The user then lies down again to return to the lying state, and the mat surface returns to the initial positions again. The process of changing from the lying state to the sitting state and back to the lying state can be recorded as one deformation process. FIG. 4b schematically illustrates the deformation of the mat surface at various detection points when the mat surface reaches the maximum change positions. The state of the elastic mat where the mat surface at the detection points is at the maximum change positions is also referred to herein as a "state of maximum change position."

Referring again to FIG. 1, at 102, an amount of energy consumed by the user when corresponding deformation is generated is determined according to the deformation information of the mat surface. For example, according to the deformation information of the mat surface recorded by the sensor and a preset method for determining the amount of energy, the elastic mat can determine the amount of energy consumed when the user does the exercise corresponding to the deformation.

In some embodiments, to determine the amount of consumed energy, an amount of work done by the user on the elastic mat at each detection point of the elastic mat is determined according to the deformation degree and the deformation duration of the mat surface at each detection point, then the sum of the amounts of work corresponding to all detection points is determined to be the amount of energy consumed by the user.

At 103, the amount of energy is recorded. For example, the elastic mat can record the determined value of consumed energy in the memory.

Figure 5:
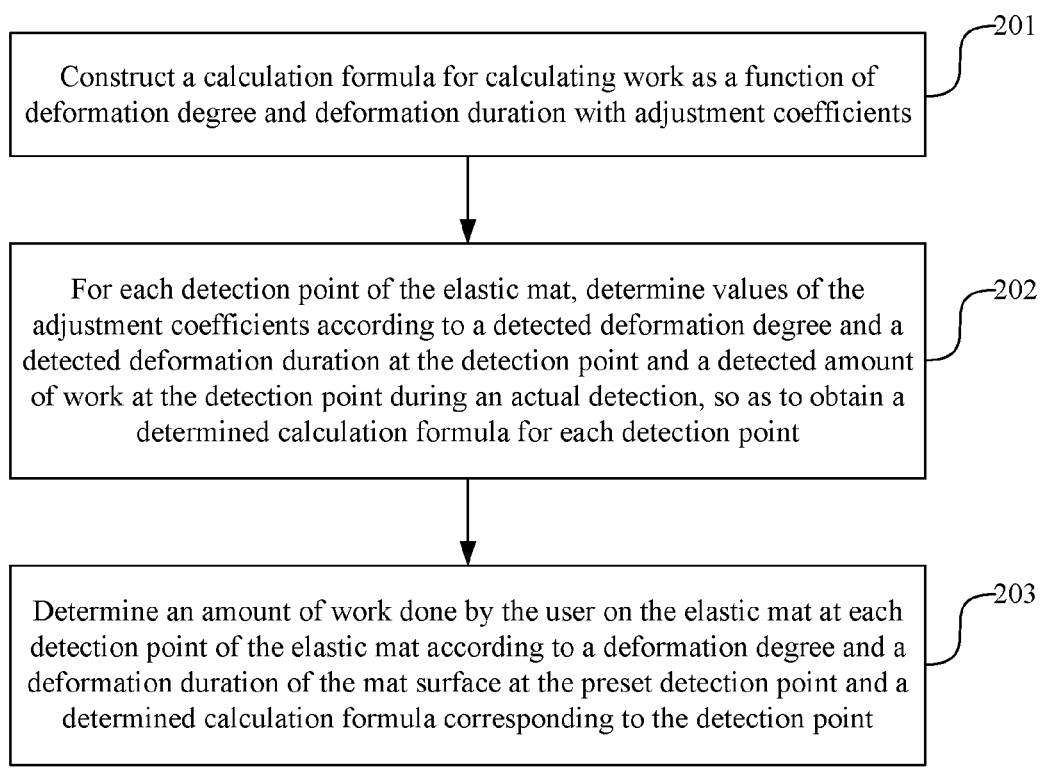
FIG. 5 is a flow chart showing a method for determining an amount of consumed energy according to another exemplary embodiment.

In some embodiments, a calculation formula can be preset to calculate the amount of energy according to the deformation information. FIG. 5 is a flow chart showing a method for calculating the amount of energy consumed by the user. As shown in FIG. 5, at 201, a calculation formula for calculating work is constructed as a function of deformation degree and deformation duration, with preset adjustment coefficients. For example, the calculation formula can take the same form for all the detection points, while different ones of the detection points may have different values of the adjustment coefficients. A calculation formula with undetermined values of adjustment coefficients may also be referred to as an "undetermined calculation formula." In some embodiments, the calculation formula may include other variables.

At 202, for each detection point of the elastic mat, values of the adjustment coefficients in the calculation formula are determined according to a detected deformation degree and a detected deformation duration at the detection point and a detected amount of work at the detection point during an actual test detection, so as to obtain a determined calculation formula corresponding to the detection point. The determined calculation formula is a particular form of the calculation formula with determined values of the adjustment coefficients.

Figure 6A:
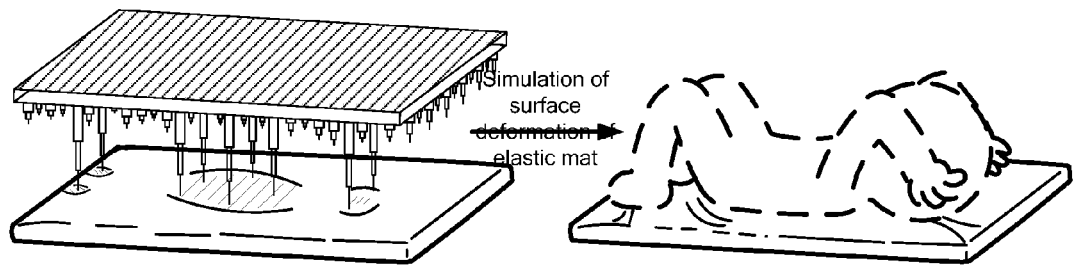
FIGS. 6a and 6b are schematic diagrams illustrating an actual test detection according to an exemplary embodiment.
Figure 6B:
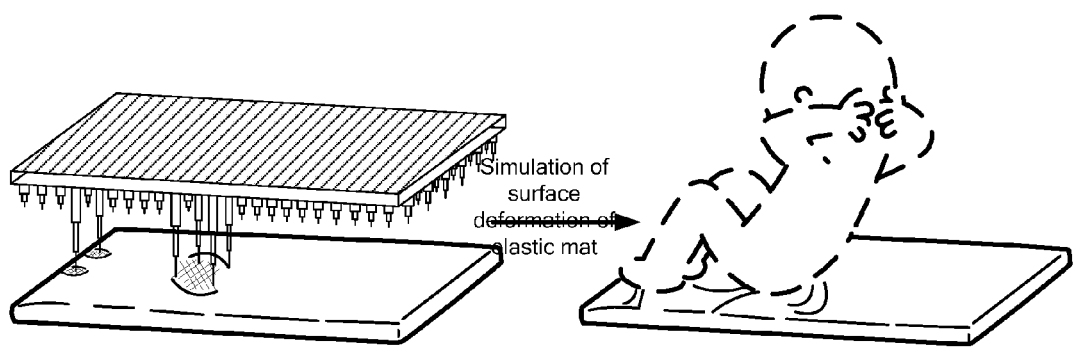

For example, a technician can do exercises on the elastic mat, such as sit-up, leg lifts, and so on. The elastic mat can record the deformation degree and the deformation duration of the mat surface at each detection point. In the meantime, the amount of energy consumed by the technician can be detected by a precise detection instrument. After the exercise, the exercise performed by the technician can be simulated by a plurality of simulation machines for exercise simulation. That is, each simulation machine presses the mat surface at a detection point according to the recorded deformation degree and deformation duration corresponding to that detection point. For example, FIGS. 6a and 6b schematically show the simulation of the surface deformation of the elastic mat of the lying state and the sitting state, respectively. After the simulation, each simulation machine can calculate, according to the amount of energy consumed by the simulation machine and a mechanical efficiency, an amount of work done by the simulation machine on the mat surface at the detection point. Subsequently, the amounts of work done by all simulation machines can be accumulated to obtain a total amount of work done by all simulation machines on the elastic mat during the simulation process.

As such, a relationship between work done by the simulation machines on the elastic mat and work done by the technician on the elastic mat can be obtained according to the total amount of work done by the simulation machines on the elastic mat and the amount of energy consumed by the technician when doing exercises. Subsequently, the work done by the technician at each detection point during the exercise can be obtained with reference to the amount of work done by each simulation machine at the same detection point. As such, values of the adjustment coefficients in the calculation formula can be determined by means of statistical fit after the actual test is performed a plurality of times, and the determined calculation formula can be obtained for each detection point.

In some embodiments, different calculation formulae can be set for different exercise types. For each exercise type, the processes for constructing the calculation formula and determining the determined calculation formula for each detection point are similar to those described above, and thus their detailed description is omitted here.

At 203, an amount of work done by the user on the elastic mat at each detection point of the elastic mat is determined according to a deformation degree and a deformation duration at the detection point and a determined calculation formula corresponding to the detection point. The sum of the amounts of work at all the detection points is determined as the amount of energy consumed when the user does the exercise corresponding to the deformation.

In some embodiments, the determined calculation formulae are chosen according to a current exercise type of the exercise being performed by the user.

In some embodiments, besides the exercise type discussed above, the determined calculation formulae can also be determined through actual detection for elastic mats with different total use times and/or made of different materials, such that the user can specifically select a corresponding calculation formula when exercising on an elastic mat.

In some embodiments, elastic mats of different types can be provided for users of different heights and/or weights. The user can also be informed of an optimal use area of an elastic mat during exercise through, for example, a manual of the elastic mat. In some embodiments, an outline can be marked on the elastic mat to notify the user that the amount of consumed energy can be most accurately detected if the user does exercises in an area defined by the outline.

In some embodiments, the current exercise type can be determined according to the deformation information of the mat surface. Specifically, different exercise types may correspond to different deformation information of the mat surface. Thus, according to detected deformation information of the mat surface, the elastic mat can determine an exercise type that is the closest to the deformation information as the current exercise type.

In some embodiments, the current exercise type can be set by the user. For example, the user can set the current exercise type on an interface of the elastic mat or on a terminal coupled with the elastic mat. As a result, the elastic mat can acquire the current exercise type according to the user's setting.

In some embodiments, the elastic mat can send a prompt signal when the amount of exercise of the user reaches a target value. For example, multiple amounts of energy can be acquired and accumulated. When the accumulated amount reaches a preset threshold, the prompt signal is sent. For example, the user can preset the threshold for the amount of energy consumed by each exercise according to, for example, body conditions of the user. When receiving an exercise start instruction inputted by the user, the elastic mat resets a previously-recorded amount of consumed energy, and records an amount of energy consumed by the user during a single deformation. Subsequently, the elastic mat accumulates amounts of energy consumed by the user during multiple deformations, and sends a prompt signal when the accumulated amount reaches the preset threshold. For example, the elastic mat can flash an indicator lamp or sound a prompt ringtone to prompt the user that the amount of energy consumed by the current exercise has reached a target value or is too high, and the user should take a break.

In some embodiments, the elastic mat can transmit the energy amount to a bound target terminal after the user finishes the exercise, so as to enable the target terminal to record statistics and display the energy amount.

Figure 7:
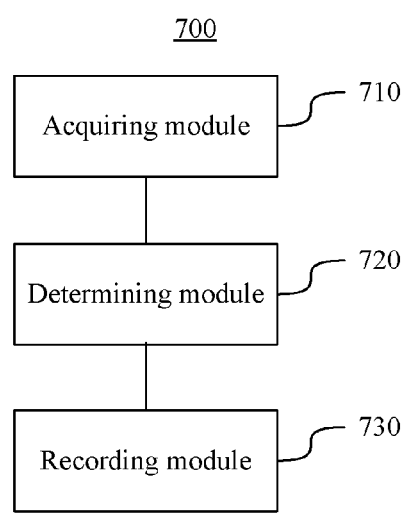
FIG. 7 is a structural diagram illustrating a device for determining an amount of consumed energy according to an exemplary embodiment.

FIG. 7 is a block diagram showing a device 700 for determining an amount of consumed energy according to an exemplary embodiment. As shown in FIG. 7, the device 700 includes an acquiring module 710, a determining module 720, and a recording module 730. The acquiring module 710 is configured to acquire deformation information of a mat surface of an elastic mat used by a user. The determining module 720 is configured to determine, according to the deformation information of the mat surface, an amount of energy consumed by the user when corresponding deformation is generated. The recording module 730 is configured to record the amount of energy.

In some embodiments, the deformation information includes a deformation degree and a deformation duration of the mat surface at each of a plurality of preset detection points of the elastic mat as, for example, described above with reference to FIGS. 3a, 3b, 4a, and 4b. As described above, the deformation degree at a detection point refers to the distance from an initial position of the mat surface at the detection point to a maximum change position of the mat surface at the detection point during one deformation process. The deformation duration refers to a duration of time that the mat surface deforms from the initial position to the maximum change position at the detection point during one deformation process.

In some embodiments, the determining module 720 is further configured to determine, according to the deformation degree and the deformation duration of the mat surface at a detection point, an amount of work done by the user on the elastic mat at the detection point of the elastic mat, and determine the sum of the amounts of work corresponding to all detection points to be the amount of energy consumed by the user.

Figure 8:
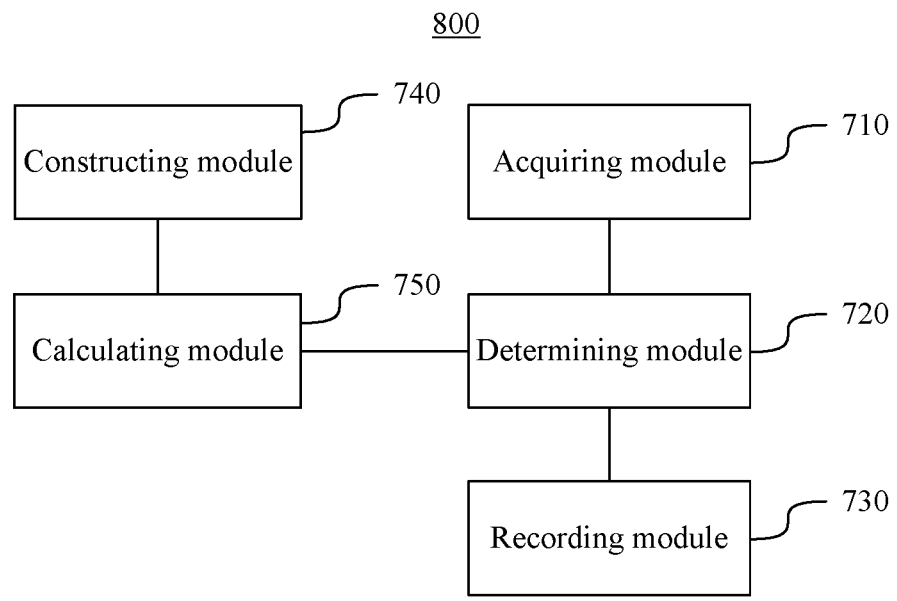
FIG. 8 is a structural diagram illustrating a device for determining an amount of consumed energy according to another exemplary embodiment.

FIG. 8 is a block diagram showing a device 800 for determining an amount of consumed energy according to another exemplary embodiment. As shown in FIG. 8, the device 800 is similar to the device 700 except that the device 800 further includes a constructing module 740 and a calculating module 750. The constructing module 740 is configured to construct a calculation formula of work on the elastic mat as a function of deformation degree and deformation durations with preset adjustment coefficients. The calculating module 750 is configured to determine, for each detection point of the elastic mat, values of the adjustment coefficients in the calculation formula according to a detected deformation degree and a detected deformation duration at the detection point and a detected amount of work at the detection point during an actual test detection, so as to obtain a determined calculation formula having determined coefficients and corresponding to the detection point.

In some embodiments, the determining module 720 is further configured to determine an amount of work done by the user on the elastic mat at each detection point of the elastic mat according to a deformation degree and a deformation duration of the mat surface at the detection point and a determined calculation formula corresponding to the detection point.

Figure 9:
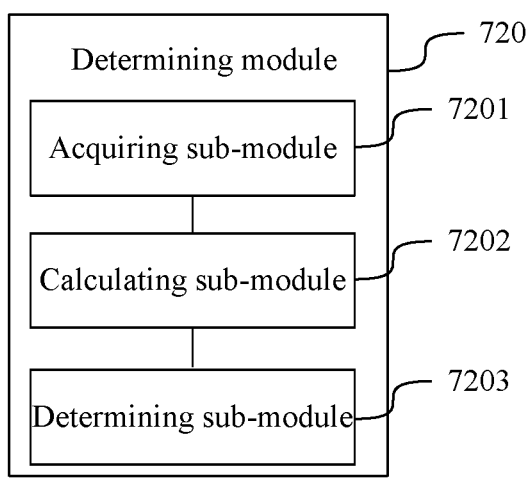
FIG. 9 is a structural diagram illustrating an example of a determining module 720 shown in FIG. 7.

FIG. 9 is a block diagram showing an example of the determining module 720. As shown in FIG. 9, the determining module 720 includes an acquiring sub-module 7201, a calculating sub-module 7202, and a determining sub-module 7203. The acquiring sub-module 7201 is configured to acquire a current exercise type. The calculating sub-module 7202 is configured to, according to a relationship among exercise type, detection point, and determined calculation formula, determine a determined calculating formula having determined coefficients and corresponding to a detection point under the current exercise type. The determining sub-module 7203 is configured to determine, according to a detected deformation degree and a detected deformation duration of the mat surface at each preset detection point and a determined calculation formula corresponding to the detection point under the current exercise type, an amount of work done by the user on the elastic mat at the detection point of the elastic mat.

In some embodiments, the acquiring sub-module 7201 is further configured to determine the current exercise type according to the deformation information of the mat surface or acquire the current exercise type set by the user.

Figure 10:
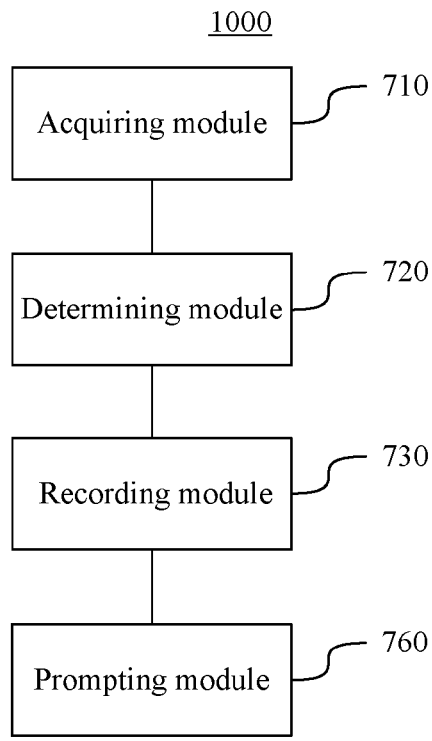
FIG. 10 is a structural diagram illustrating a device for determining an amount of consumed energy according to another exemplary embodiment.

FIG. 10 is a block diagram showing a device 1000 for determining an amount of consumed energy according to another exemplary embodiment. As shown in FIG. 10, the device 1000 is similar to the device 700, except that the device 1000 further includes a prompting module 760 configured to accumulate amounts of energy acquired over time and, when the accumulated amount reaches a preset threshold, send a prompt signal.

Figure 11:
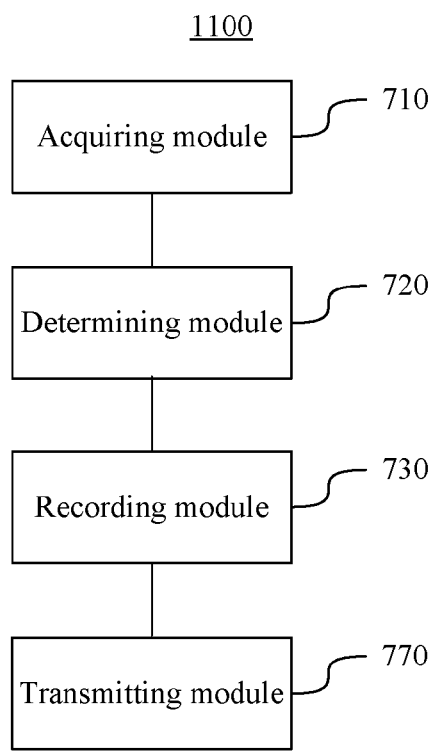
FIG. 11 is a structural diagram illustrating a device for determining an amount of consumed energy according to another exemplary embodiment.

FIG. 11 is a block diagram showing a device 1100 for determining an amount of consumed energy according to another exemplary embodiment. As shown in FIG. 11, the device 1100 is similar to the device 700, except that the device 1100 further includes a transmitting module 770 configured to transmit the energy amount to a bound target terminal to enable the target terminal to record statistics and display the energy amount.

Operations of the above-described exemplary devices are similar to the above-described exemplary methods, and thus their detailed description is omitted here.

In the above-described exemplary devices, the functional modules are exemplary. The functions of these modules can be completed by different modules as required. That is, the internal structures of the exemplary devices can be divided into different functional modules to complete all or some functions described above.

Figure 12:
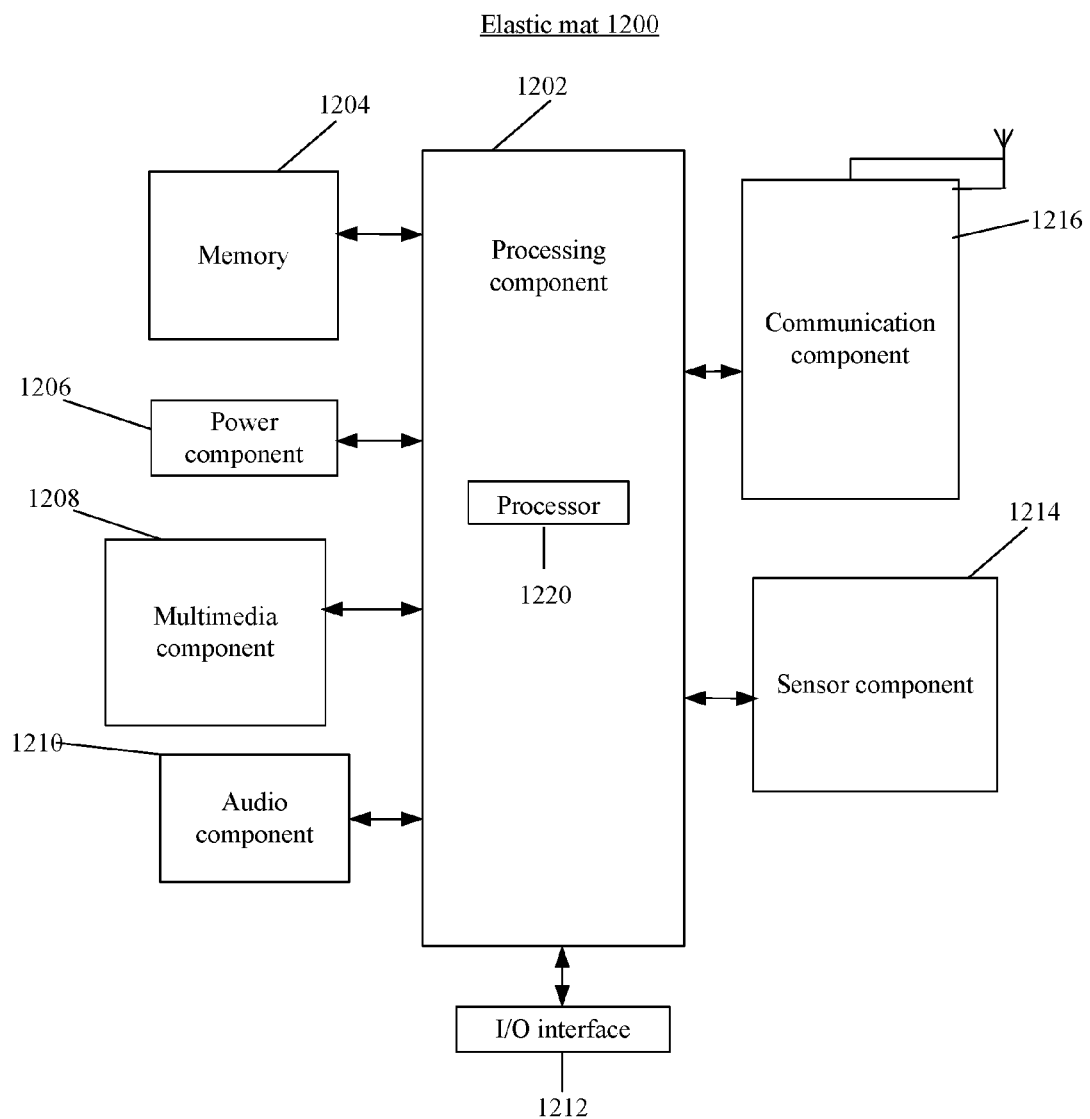
FIG. 12 is a structural diagram illustrating an elastic mat according to an exemplary embodiment.

FIG. 12 is a block diagram showing an elastic mat 1200 according to an exemplary embodiment. The elastic mat 1200 can be, for example, an intelligent mattress. The elastic mat 1200 includes one or more of the following components: a processing component 1202, a memory 1204, a power component 1206, a multimedia component 1208, an audio component 1210, an Input/Output (I/O) interface 1212, a sensor component 1214 and a communication component 1216.

Generally, the processing component 1202 controls overall operations of the elastic mat 1200, such as operations associated with displaying and recording operations. The processing component 1202 may include one or more processors 1220 to execute instructions so as to complete all or part of the steps of the abovementioned methods. Moreover, the processing component 1202 may include one or more modules which facilitate interaction between the processing component 1202 and other components. For example, the processing component 1202 may include a multimedia module so as to facilitate interaction between the multimedia component 1208 and the processing component 1202.

The memory 1204 is configured to store various types of data to support the operations in the elastic mat 1200. Examples of these data include instructions for any applications or methods operated on the elastic mat 1200 and so on. The memory 1204 may be implemented by a volatile or non-volatile storage device of any type or a combination thereof, such as a Static Random-Access Memory (SRAM), an Electrically Erasable Programmable Read-Only Memory (EEPROM), an Erasable Programmable Read-Only Memory (EPROM), a Programmable Read-Only Memory (PROM), a Read-Only Memory (ROM), a magnetic memory, a flash memory, a magnetic disk or an optical disk.

The power component 1206 provides power for various components of the elastic mat 1200. The power component 1206 may include a power source management system, one or more power supplies, and other components associated with generation, management and distribution of power for the elastic mat 1200.

The multimedia component 1208 includes a screen providing an output interface between the elastic mat 1200 and a user. In some embodiments, the screen may include a Liquid Crystal Display (LCD) and a touch panel. If the screen includes the touch panel, the screen may be implemented as a touch screen to receive an input signal from the user. The touch panel includes one or more touch sensors to sense touches, swipes and gestures on the touch panel. The touch sensor may not only sense a boundary of a touch or swipe action, but also detect a duration and a pressure related to the touch or swipe action. In some embodiments, the multimedia component 1208 may include a front camera and/or a rear camera. When the elastic mat 1200 is in an operation mode, such as a camera mode or a video mode, the front camera and/or the rear camera may receive external multimedia data. Each front camera and each rear camera may be a fixed optical lens system or may be provided with focusing and optical zooming capabilities.

The audio component 1210 is configured to output and/or input an audio signal. For example, the audio component 1210 includes a microphone. When the elastic mat 1200 is in an operation mode, such as a playing mode, a recording mode and a voice recognition mode, the microphone is configured to receive an external audio signal. The received audio signal may be further stored in the memory 1204 or sent by the communication component 1216.

The I/O interface 1212 provides an interface between the processing component 1202 and a peripheral interface module. The peripheral interface module may be a keyboard, a click wheel, a button and so on. The button may include, but not limited to a home button, a volume button, a starting button and a locking button.

The sensor component 1214 includes one or more sensors configured to provide status assessment in various aspects for the elastic mat 1200. For example, the sensor component 1214 may detect an on/off state of the elastic mat 1200, and relative positioning of the components, such as a display and a keypad of the elastic mat 1200. The sensor component 1214 may further detect a change in a position of the elastic mat 1200 or a component of the elastic mat 1200, presence or absence of a contact between the user and the elastic mat 1200, orientation or acceleration/deceleration of the elastic mat 1200 and a change in temperature of the elastic mat 1200. The sensor component 1214 may include a proximity sensor configured to detect presence of an object nearby without any physical contact. The sensor component 1214 may further include an optical sensor, such as a Complementary Metal Oxide Semiconductor (CMOS) or Charge Coupled Device (CCD) image sensor used in an imaging application. In some embodiments, the sensor component 1214 may further include an acceleration sensor, a gyroscope sensor, a magnetic sensor, a pressure sensor or a temperature sensor.

The communication component 1216 is configured to facilitate wired or wireless communication between the elastic mat 1200 and other devices. The elastic mat 1200 may access a wireless network based on a communication standard, such as a Wireless Fidelity (WiFi) network, the second Generation (2G), the third Generation (3G) network, or the fourth Generation (4G) network, or a combination thereof. In an exemplary embodiment, the communication component 1216 receives a broadcast signal from an external broadcast management system or broadcasts related information through a broadcast channel. In an exemplary embodiment, the communication component 1216 further includes a Near Field Communication (NFC) module to facilitate short-range communication. For example, the NFC module may be implemented based on a Radio-frequency Identification (RFID) technology, an Infrared Data Association (IrDA) technology, an Ultra Wide Band (UWB) technology, a Bluetooth technology and other technologies.

In an exemplary embodiment, the elastic mat 1200 may be implemented by one or more Application Specific Integrated Circuits (ASICs), Digital Signal Processors (DSPs), Digital Signal Processing Devices (DSPDs), Programmable Logic Devices (PLDs), Field Programmable Gate Arrays (FPGAs), controllers, microcontrollers, microprocessors, or other electronic components, so as to execute the abovementioned method.

In an exemplary embodiment, there is also provided a non-transitory computer-readable storage medium including instructions, such as the memory 1204 including instructions. The instructions may be executed by the processor 1220 of the elastic mat 1200 to implement a method consistent with the present disclosure, such as one of the above-described exemplary methods. For example, the non-transitory computer readable storage medium may be a ROM, a Compact Disc-ROM (CD-ROM), a magnetic tape, a floppy disk, an optical data memory and so on.

Other implementation solutions of the present disclosure will be apparent to those skilled in the art from consideration of the specification and practice of the present disclosure. The application aims to cover any variations, uses or adaptive changes of the present disclosure. These variations, uses or adaptive changes follow general principles of the present disclosure and include such departures from the disclosure as common general knowledge or conventional technical means in the art. The specification and embodiments are only considered exemplary, and the scope and spirit of the disclosure will be indicated by the following claims.

It should be understood that the present disclosure is not limited to the precise structures that have been described above or illustrated in the accompanying drawings, and various modifications and changes may be made without departing from the scope of the present disclosure. The scope of the present disclosure is limited by the appended claims.

INDUSTRIAL APPLICATION

In the embodiments of the present disclosure, deformation information of the surface of an elastic mat is acquired; an amount of energy consumed by a user when corresponding deformation is generated is determined according to the deformation information of the surface of the elastic mat; and the amount of energy is recorded. As such, the accuracy in calculating the amount of energy consumed during an exercise can be improved.

What is claimed is:

1. A method for determining an amount of consumed energy, comprising:
   acquiring deformation information of a mat surface of an elastic mat used by a user during one deformation process;
   determining, according to the deformation information, an amount of energy consumed by the user during the deformation process; and
   recording the amount of energy,
   wherein acquiring the deformation information includes, for each of a plurality of detection points of the elastic mat:
   acquiring a deformation degree and a deformation duration of the mat surface at the detection point, the deformation degree being a distance from an initial position of the mat surface at the detection point to a maximum change position of the mat surface at the detection point during the deformation process, and the deformation duration being a period of time during which the mat surface at the detection point is deformed from the initial position to the maximum change position during the deformation process.

2. The method according to claim 1, wherein determining the amount of energy consumed by the user includes:
   determining, for each of the detection points, an amount of work done by the user on the elastic mat at the detection point according to the deformation degree and the deformation duration of the mat surface at the detection point; and
   determining a sum of the amounts of work corresponding to the detection points as the amount of energy consumed by the user.

3. The method according to claim 2, further comprising:
   constructing an undetermined calculation formula for calculating work as a function of deformation degree and deformation duration with at least one adjustment coefficient; and
   determining, for each of the detection points, a value of each of the at least one adjustment coefficient according to a test deformation degree and a test deformation duration of the detection point and a test amount of the work measured during a test detection, so as to obtain a determined calculation formula corresponding to the detection point, the determined calculation formula having the determined at least one adjustment coefficient.

4. The method according to claim 3, wherein determining the amount of work for each of the detection points includes:
   determining the amount of work by substituting the deformation degree and the deformation duration of the detection point into the determined calculation formula corresponding to the detection point.

5. The method according to claim 3, wherein:
   constructing the undetermined calculation formula includes:
   constructing undetermined calculation formulae, each of which corresponds to one of a plurality of exercise types, each of the undetermined calculation formulae having at least one corresponding adjustment coefficient, and determining the value of each of the at least one adjustment coefficient includes:
acquiring a current exercise type;
selecting one of the undetermined calculation formulae according to the current exercise type; and
determining, for each of the detection points, a value of each of the at least one corresponding adjustment coefficient in the selected undetermined calculation formula to obtain the determined calculation formula corresponding to the detection point and the current exercise type.

6. The method according to claim 5, wherein acquiring the current exercise type includes:
determining, according to the deformation information, the current exercise type; or
acquiring the current exercise type set by the user.

7. The method according to claim 1, further comprising:
accumulating the amount of energy over time to obtain an accumulated energy amount; and
sending, when the accumulated energy amount reaches a preset threshold, a prompt signal.

8. The method according to claim 1, further comprising, after recording the amount of energy:
transmitting the amount of energy to a bound target terminal to enable the target terminal to record statistics and display the amount of energy.

9. An elastic mat, comprising:
a processor; and
a memory storing instructions that, when executed by the processor, cause the processor to:
acquire deformation information of a mat surface of the elastic mat used by a user during one deformation process;
determine, according to the deformation information, an amount of energy consumed by the user during the deformation process; and
record the amount of energy,
wherein the instructions further cause the processor to, for each of a plurality of detection points of the elastic mat:
acquire a deformation degree and a deformation duration of the mat surface at the detection point, the deformation degree being a distance from an initial position of the mat surface at the detection point to a maximum change position of the mat surface at the detection point during the deformation process, and the deformation duration being a period of time during which the mat surface at the detection point is deformed from the initial position to the maximum change position during the deformation process.

10. The elastic mat according to claim 9, wherein the instructions further cause the processor to:
determine, for each of the detection points, an amount of work done by the user on the elastic mat at the detection point according to the deformation degree and the deformation duration of the mat surface at the detection point; and
determine a sum of the amounts of work corresponding to the detection points as the amount of energy consumed by the user.

11. The elastic mat according to claim 10, wherein the instructions further cause the processor to:
construct an undetermined calculation formula for calculating work as a function of deformation degree and deformation duration with at least one adjustment coefficient; and
determine, for each of the detection points, a value of each of the adjustment coefficient according to a test deformation degree and a test deformation duration of the detection point and a test amount of the work measured during a test detection, so as to obtain a determined calculation formula corresponding to the detection point, the determined calculation formula having the determined at least one adjustment coefficient.

12. The elastic mat according to claim 11, wherein the instructions further cause the processor to:
determine the amount of work by substituting the deformation degree and the deformation duration of the detection point into the determined calculation formula corresponding to the detection point.

13. The elastic mat according to claim 11, wherein the instructions further cause the processor to:
construct undetermined calculation formulae, each of which corresponds to one of a plurality of exercise types, each of the undetermined calculation formulae having at least one corresponding adjustment coefficient;
acquire a current exercise type;
select one of the undetermined calculation formulae according to the current exercise type; and
determine, for each of the detection points, a value of each of the at least one adjustment coefficient in the selected undetermined calculation formula to obtain the determined calculation formula corresponding to the detection point and the current exercise type.

14. The elastic mat according to claim 13, wherein the instructions further cause the processor to:
determine, according to the deformation information, the current exercise type; or
acquire the current exercise type set by the user.

15. The elastic mat according to claim 9, wherein the instructions further cause the processor to:
accumulate the amount of energy over time to obtain an accumulated energy amount; and
send, when the accumulated energy amount reaches a preset threshold, a prompt signal.

16. The elastic mat according to claim 9, wherein the instructions further cause the processor to, after recording the amount of energy:
transmit the amount of energy to a bound target terminal to enable the target terminal to record statistics and display the amount of energy.

17. A non-transitory computer-readable storage medium having stored therein instructions that, when executed by a processor of an elastic mat, cause the elastic mat to:
acquire deformation information of a mat surface of the elastic mat used by a user during one deformation process;
determine, according to the deformation information, an amount of energy consumed by the user during the deformation process; and
record the amount of energy,
wherein the instructions further cause the processor to, for each of a plurality of detection points of the elastic mat:
acquire a deformation degree and a deformation duration of the mat surface at the detection point, the deformation degree being a distance from an initial position of the mat surface at the detection point to a maximum change position of the mat surface at the detection point during the deformation process, and the deformation duration being a period of time during which the mat surface at the detection point is deformed from the initial position to the maximum change position during the deformation process.

* * * * *